US007875868B2

(12) United States Patent
Moriyama et al.

(10) Patent No.: US 7,875,868 B2
(45) Date of Patent: Jan. 25, 2011

(54) CHARGED PARTICLE BEAM IRRADIATION SYSTEM

(75) Inventors: Kunio Moriyama, Hitachi (JP);
Takahide Nakayama, Nara (JP);
Hideaki Nishiuchi, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 225 days.

(21) Appl. No.: 12/336,592

(22) Filed: Dec. 17, 2008

(65) Prior Publication Data

US 2009/0184263 A1 Jul. 23, 2009

(30) Foreign Application Priority Data

Dec. 21, 2007 (JP) ............................. 2007-330297

(51) Int. Cl.
*A61N 5/00* (2006.01)
(52) U.S. Cl. .................................... 250/492.3; 250/398
(58) Field of Classification Search .............. 250/492.3, 250/398
See application file for complete search history.

(56) References Cited

U.S. PATENT DOCUMENTS 5,260,581 A 11/1993 Lesyna et al.
5,363,008 A 11/1994 Hiramoto et al.
7,432,516 B2 * 10/2008 Peggs et al. .............. 250/492.3

FOREIGN PATENT DOCUMENTS

EP 0 779 081 A2 6/1997
JP 2833602 10/1998

OTHER PUBLICATIONS

Chu et al., "Instrumentation for treatment of cancer using proton and light-ion beams", Review of Scientific Instruments, vol. 64, No. 8 (Aug. 1993) p. 2074-2093.
Proceedings of the Symposium on Accelerator and Related Technology for Application, vol. 7 (Jun. 2005) p. 35-36.

\* cited by examiner

*Primary Examiner*—Kiet T Nguyen
(74) *Attorney, Agent, or Firm*—Antonelli, Terry, Stout & Kraus, LLP.

(57) ABSTRACT

A charged particle beam irradiation system comprises a high-speed steerer (beam dump device) 100 disposed in a course of a beam transport line 4 through which an ion beam is extracted from a charged-particle beam generator 1. The beam dump device 100 is provided with dose monitoring devices 105, 106 for measuring a dose of an ion beam applied to a beam dump 104 so that the intensity of the ion beam can be measured without transporting the ion beam to irradiation nozzles 15A through 15D. Thus, the system is capable of adjusting the intensity of an ion beam extracted from a synchrotron without operating each component of a beam transport line, and an irradiation nozzle.

9 Claims, 7 Drawing Sheets

CHARGED PARTICLE BEAM IRRADIATION SYSTEM

BACKGROUND OF THE INVENTION

1. Field of the Invention

The present invention relates to a charged particle beam irradiation system. More particularly the invention relates to a charged particle beam irradiation system that is preferably applied to a particle beam therapy system for treating an affected part by irradiating the affected part with a charged particle beam such as a proton and a carbon ion.

2. Description of the Related Art

A treatment method which irradiates an affected part of a patient (for example, cancer) with a charged particle beam (ion beam) such as a proton and a carbon ion is known. A charged particle beam irradiation system used for the treatment (a particle beam extraction device or a charged particle beam extraction device) includes an ion beam generator. An ion beam accelerated by the ion beam generator passes through a first beam transport line, and a second beam transport line that is disposed in a rotating gantry, and then reaches an irradiation nozzle disposed in the rotating gantry. The ion beam is extracted from the irradiation nozzle, and the affected part of the patient is then irradiated with the ion beam. As the ion beam generator, for example, a synchrotron (circular accelerator) as described in U.S. Pat. No. 5,363,008 is known. This synchrotron includes: means for causing a charged particle beam to orbit around a closed orbit; means for bringing betatron oscillations of the charged particle beam into a resonance state outside a stability limit of resonance; and an extraction deflector for taking out the charged particle beam from the closed orbit.

An irradiation nozzle shapes the ion beam introduced by the ion beam generator on the basis of the depth from a body surface of the patient and a shape of the affected part, and then irradiates the affected part of the patient on a treatment bed with the ion beam. In general, an irradiation nozzle irradiates an affected part with an ion beam by using any of the following beam irradiation methods: double passive irradiation (non-patent literature 1, p 2081, FIG. 35); Wobbler method (non-patent literature 1, p 2084, FIG. 41); and beam scanning method (Japanese Patent No. 2596292 and non-patent literature 1, p 2092-2093).

An affected part usually has substantial thickness in a traveling direction of an ion beam in a body of a patient. In order to irradiate the affected part with an ion beam over the whole thickness of the affected part, the energy of the ion beam must be controlled so as to form a uniform absorbed dose range, which is wide to some extent, in the traveling direction of the ion beam (that is to say, Spread-Out Bragg Peak; hereinafter referred to as "SOBP"). As energy control means for forming desired SOBP, an irradiation method which adopts Range Modulation Wheel (hereinafter referred to as "RMW") is proposed (non-patent literature 1, p 2077, FIG. 30). The RMW is a rotational structure in which a plurality of wedge-shaped energy absorbing materials are disposed in a circumference direction so that the thickness of a region through which an ion beam passes changes in point of time. The RMW is so devised that the rotation of the RMW causes the thickness in an ion beam traveling direction (in an axial direction of the RMW) to increase or decrease. Such an irradiation method which uses the RMW is designated as "RMW irradiation method".

On the other hand, when a charged particle irradiation system is used, there is a possibility that some of charged particle beams extracted from an ion beam generator will not be transported to the charged particle irradiation system. This kind of beams is treated as unnecessary charged particle beams. For this reason, in order to handle the unnecessary charged particle beams, a first beam transport line is provided with a beam dump device (U.S. Pat. No. 5,260,581).

Non-patent literature 1: REVIEW OF SCIENTIFIC INSTRUMENTS, Volume 64, Number 8 (August, 1993) p 2074-2093

Non-patent literature 2: Proceedings of the Symposium on Accelerator and Related Technology for Application, Volume 7 (June, 2005) p 35-36.

SUMMARY OF THE INVENTION

The synchrotron accelerates an ion beam injected from a pre-accelerator up to desired energy before the ion beam is extracted. One operation cycle of the synchrotron is constituted of injection, acceleration, extraction, and deceleration. The synchrotron operates by repeating this operation cycle. Therefore, in contrast to cyclotrons, an ion beam is supplied to a synchrotron only at the time of injection in one operation cycle. The accumulated amount of ion beams accelerated by the synchrotron decreases, from the maximum value achieved at the end of the acceleration, with the lapse of the time in the extraction control (non-patent literature 1). Moreover, it is known that the relationship between the amplitude (voltage) of a radiofrequency signal to be applied to an radiofrequency-wave applicator electrode and the intensity of an ion beam extracted from the synchrotron also influences the accumulated amount of ion beams in the synchrotron. Therefore, it is not easy to extract an ion beam at the desired intensity.

Heretofore, there is proposed an extracted-beam intensity control method including the steps of: modeling an extraction process in consideration of scattering of an ion beam caused by an extraction radiofrequency signal to be applied to the ion beam; estimating the intensity of an ion beam orbiting the synchrotron from the number of particles extracted by a requested beam intensity signal; optimizing a pattern for determining an amplitude modulation function of a radiofrequency signal on the basis of the intensity to determine a corresponding intensity pattern; and controlling the intensity of an extracted beam on the basis of the intensity pattern (for example, non-patent literature 2). However, the intensity of the extraction beam does not always follow the intensity pattern that has been estimated. For example, even if a beam extraction pattern having a uniform structure is intended to be acquired, an intensity pattern having a time structure, which cannot be said to be a uniform structure, is obtained.

In addition, the dosimeter for measuring the intensity of a beam is disposed on the irradiation nozzle side. Accordingly, the intensity of the beam extracted from the synchrotron cannot be measured before the dosimeter receives the beam that has passed through a transportation line, a gantry, and the irradiation nozzle.

Therefore, in a construction stage of the charged particle beam irradiation system, the intensity of an ion beam extracted from the synchrotron could not be measured until the completion of the irradiation nozzle. Moreover, even after the construction of the charged particle beam irradiation system is completed, if an abnormal state of the intensity of an extracted beam is detected, it is not possible to easily judge whether the abnormal state is caused by the extracted beam of the synchrotron or by a malfunction of an element disposed after the synchrotron, which requires a long period of time to investigate the cause.

In the case of the system in which the first beam transport line is provided with the beam dump device (described in U.S.

Pat. No. 5,260,581), if some of charged particle beams extracted from the ion beam generator result in unnecessary beams, the unnecessary beams are transported to the beam dump so that the unnecessary beams can be properly handled. However, the beam dump device in the conventional system is only used to dump unnecessary beams.

An object of the present invention is to provide a charged particle beam irradiation system that is capable of adjusting the intensity of an ion beam extracted from a synchrotron without operating each component of a beam transport line, and an irradiation nozzle.

In order to achieve the above-described object, the present invention has such characteristics that a beam dump device is disposed in a course of a beam transport line through which an ion beam is extracted from an ion beam generator, and that a dose monitoring device for measuring a dose of a charged particle beam applied to a beam dump is disposed in the beam dump device so that the intensity of the ion beam can be measured without transporting the ion beam to an irradiation nozzle.

It is desirable to dispose the beam dump device, which is provided with the dose monitoring device, at a position immediately after the synchrotron so that an ion beam can reach the beam dump device without passing through many devices of the beam transport line.

According to the present invention, the intensity of an ion beam extracted from a synchrotron can be adjusted without operating each component of a beam transport line and an irradiation nozzle.

This makes it possible to perform accurate adjustment with fluctuation factors of the intensity of the extracted ion beam correctly kept track of.

In addition, when an extracted ion beam fluctuates for some unexpected reason, a fluctuation factor thereof can be identified. To be more specific, it is possible to judge whether the fluctuation factor exists in the synchrotron or in the other elements including the beam transport line, the irradiation nozzles, and other devices. Therefore, saving of time taken to cope with the fluctuation factor and an improvement in accuracy can be expected.

Moreover, in the construction stage of a charged particle beam irradiation system, the intensity of the ion beam extracted from the synchrotron can be adjusted without waiting until the construction of the charged particle beam irradiation system is completed. This enables early startup of the charged particle beam irradiation system.

BRIEF DESCRIPTION OF THE DRAWINGS

FIGS. 3A through 3C are charts each illustrating how a synchrotron operates in one operation cycle.

FIGS. 7A through 7C are charts each illustrating how a synchrotron operates in one operation cycle when irradiation with an ion beam is carried out by means of spot scanning.

DESCRIPTION OF THE PREFERRED EMBODIMENTS

Preferred embodiments of the present invention will now be described.

A first embodiment of the present invention is described with reference to FIGS. 1 through 5.

Figure 1:
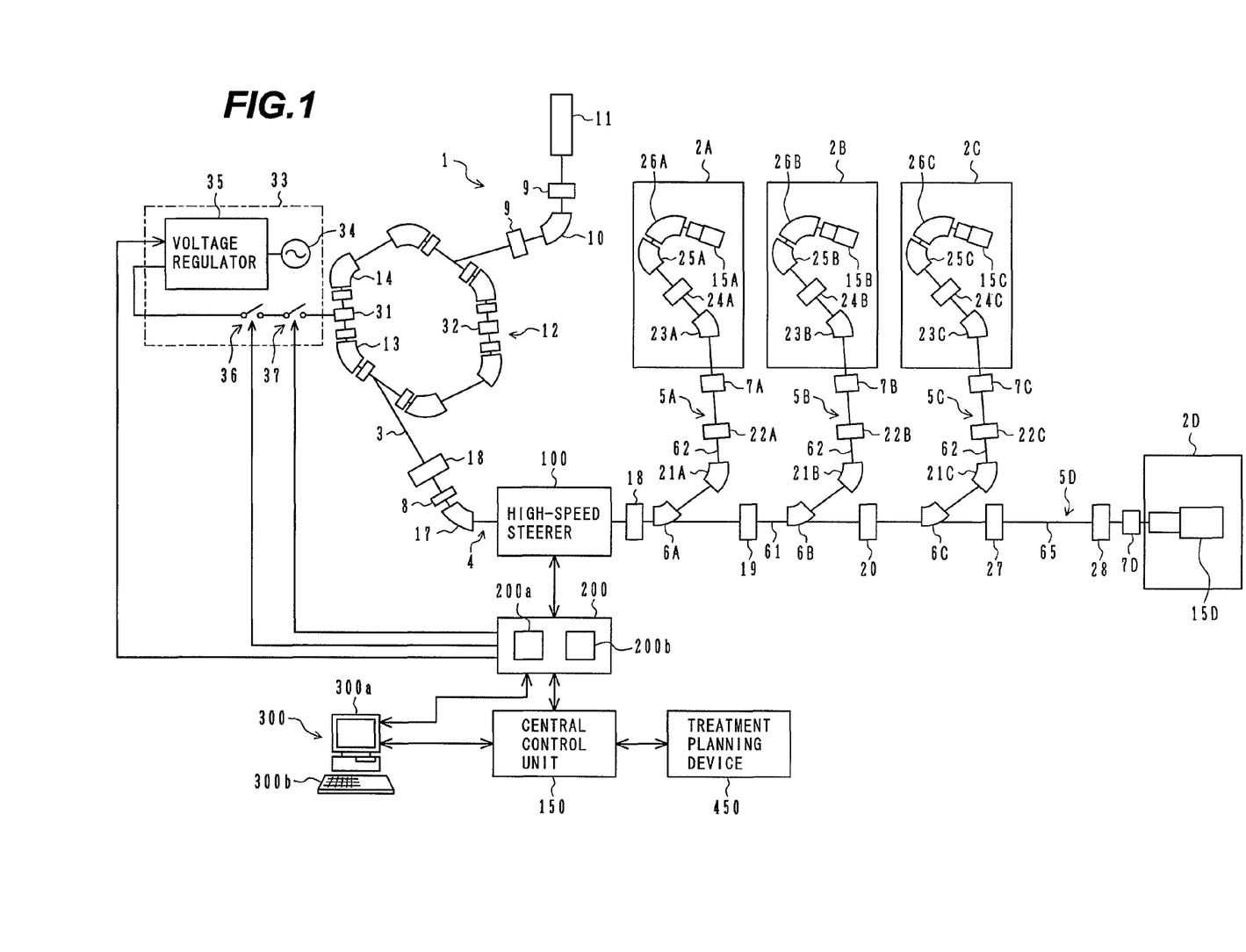
FIG. 1 is a diagram schematically illustrating an overall configuration of a charged particle beam irradiation system according to a first embodiment of the present invention.

As shown in FIG. 1, a charged particle beam irradiation system according to the first embodiment includes: a charged-particle (ion) beam generator 1; a first beam transport line 4 provided downstream of the charged-particle beam generator 1; second beam transport lines 5A, 5B, 5C, and 5D, which branch from the first beam transport line 4; switching magnets (path selectors) 6A, 6B, and 6C; and irradiation nozzles 15A, 15B, 15C, and 15D that are irradiation devices. The first beam transport line 4 is a common beam transport line that introduces an ion beam to each of the second beam transport lines 5A, 5B, 5C, and 5D. The second beam transport lines 5A, 5B, 5C, and 5D are provided for the irradiation nozzles 15A, 15B, 15C, and 15D, respectively. The irradiation nozzles 15A, 15B, 15C, and 15D are located in treatment rooms 2A, 2B, 2C, and 2D, respectively. The charged particle beam irradiation system according to the first embodiment is a proton-beam therapy system.

The charged-particle beam generator 1 includes an ion source (not illustrated), a pre-accelerator (for example, a linear accelerator) 11, and a synchrotron 12 that is a main accelerator. The synchrotron 12 has both of a radiofrequency-wave applicator 31 and a radiofrequency cavity (acceleration system) 32 located on the closed orbit of an ion beam. The radiofrequency-wave applicator 31 includes a pair of radiofrequency-wave applicator electrodes (not illustrated), which are connected to a radiofrequency-wave supply unit 33 used for extraction of radiofrequency waves. The radiofrequency-wave supply unit 33 includes a radiofrequency oscillator (radiofrequency power supply) 34, a voltage regulator (beam intensity control unit) 35, an interlock switch (switching device) 36, and an irradiation control switch (open/close switch) 37. The interlock switch 36 is opened by an interlock signal; it is kept closed under normal conditions. The irradiation control switch 37 is closed by a beam extraction start signal and is opened by a beam extraction stop signal. The radiofrequency-wave applicator 31 is supplied with radiofrequency voltage from the radiofrequency oscillator 34 through the voltage regulator 35 and the switches 36 and 37. Another radiofrequency power supply (not illustrated) is separately provided for applying radiofrequency power to the radiofrequency cavity 32.

Ions generated by the ion source (for example, positive ions or carbon ions) are accelerated by the pre-accelerator 11. The ion beam (charged particle beam) extracted from the pre-accelerator 11 is injected into the synchrotron 12. The ion beam is then energized and accelerated under the influence of an electromagnetic field in the radiofrequency cavity 32 generated by applying the radiofrequency power to the radiofrequency cavity 32 from the radiofrequency power supply that is provided for the radiofrequency cavity 32. The ion beam orbiting in the synchrotron 12 is accelerated up to a predetermined energy (for example, up to a value between 100 and 200 MeV). After that, the open/close switch 37 is closed. As a result, the extraction radiofrequency-wave applicator 31 applies, to the orbiting ion beam, a radiofrequency wave received from the radiofrequency oscillator 34 that is the other radiofrequency power supply. This causes the ion beam orbiting within a stability limit to go beyond the stability limit; consequently, the ion beam is extracted though an extraction deflector. When the ion beam is extracted, electric current applied to a quadrupole magnet 13 and a bending magnet 14, which are included in the synchrotron 12, is kept at a predetermined value; its stability limit is also kept substantially constant. By opening the open/close switch 37 to stop the application of the radiofrequency power to the extraction radiofrequency-wave applicator 31, the extraction of the ion beam from the synchrotron 12 is stopped.

The ion beam extracted from the synchrotron 12 is transported through the first beam transport line 4 to the downstream side through a high-speed steerer 100 (described later). The first beam transport line 4 includes: a beam path 3; and a quadrupole magnet 18, a shutter 8, a bending magnet 17, a quadrupole magnet 18, a switching magnet 6A, and a beam path 61, which are disposed in the beam path 3 in this order from the upstream side of the beam traveling direction. The first beam transport line 4 further includes a quadrupole magnet 19, a switching magnet 6B, a quadrupole magnet 20, and a switching magnet 6C, which are also disposed in the beam path 3 in this order from the upstream side of the beam traveling direction. The ion beam extracted into the first beam transport line 4 is selectively introduced into either of the second beam transport lines 5A, 5B, 5C, or 5D by the deflecting (or non-deflecting) functions of the switching magnets 6A, 6B, and 6C, which are induced by exciting (or not exciting) the magnets.

The second beam transport line 5A includes: a beam path 62 that is connected to the beam path 3 of the first beam transport line 4 and communicates with the irradiation nozzle 15A located in the treatment room 2A; and a bending magnet 21A, a quadrupole magnet 22A, a shutter 7A, a bending magnet 23A, a quadrupole magnet 24A, a bending magnet 25A, and a bending magnet 26A, which are disposed in the beam path 62 in this order from the upstream side of the beam traveling direction.

The second beam transport line 5B and 5C are also configured in the same manner as the second beam transport line 5A is. Reference numbers denoting the same components on the second beam transport line 5B and 5C as on 5A are followed by the letters B and C, respectively, instead of the letter A. The second beam transport line 5D includes: a beam path 65 that is connected to the beam path 61 of the first beam transport line 4 and communicates with the irradiation nozzle 15D located in the treatment room 2D; and quadrupole magnets 27 and 28 and a shutter 7D, which are disposed in the beam path 65 in this order from the upstream side of the beam traveling direction.

By exciting the corresponding electromagnet (switching magnet 6A), the ion beam introduced into the second beam transport line 5A through the first beam transport line 4 is transported through the beam path 62 to the irradiation nozzle 15A. In a similar manner, ion beams introduced into the second beam transport lines 5B and 5C are transported to the irradiation nozzles 15B and 15C, respectively, through the respective beam paths 62; an ion beam introduced to the second beam transport line 5D is transported through the beam path 65 to the irradiation nozzle 15D.

Each of the irradiation nozzles 15A through 15C is attached to one of the rotating gantries (not illustrated) located in the treatment rooms 2A through 2C, respectively. The irradiation nozzle 15D is a stationary type irradiation nozzle.

Each of the irradiation nozzles 15A through 15C forms a uniform dose distribution in the lateral direction (the direction perpendicular to the ion beam traveling direction). An ion beam, therefore, is spread out in the lateral direction by the double passive irradiation method to irradiate an affected part of a patient. In addition, each of the irradiation nozzles 15A through 15C includes a range modulation wheel (RMW) as energy control means for forming a desired SOBP. During the rotation of the RMW, an ion beam passing through the RMW is ON/OFF controlled within a specified angle range. In order to carry out such ion-beam ON/OFF control, each of the irradiation nozzles 15A through 15C further includes: means for detecting the rotation angle of the RMW (for example, an encoder); and a dosimeter for detecting the dose (radiation amount) of the ion beam that has passed through the RMW. The obtained angle information and dose information are output to an acceleration/irradiation control unit 200 (described later).

The charged particle beam irradiation system according to this embodiment further includes a high-speed beam steerer (charged particle beam dump) 100 that is disposed on the first beam transport line 4. By controlling the high-speed steerer 100, an ion beam extracted into the first beam transport line 4 can be transported to the subsequent second beam transport lines 5B, 5C, or 5D or dumped (absorbed) into a beam dump in the high-speed steerer 100. The high-speed steerer 100 is placed at a position on the first beam transport line 4 which is immediately downstream of the synchrotron 12 so that an ion beam can reach the high-speed steerer 100 without passing through many devices on the beam transport line.

Figure 2:
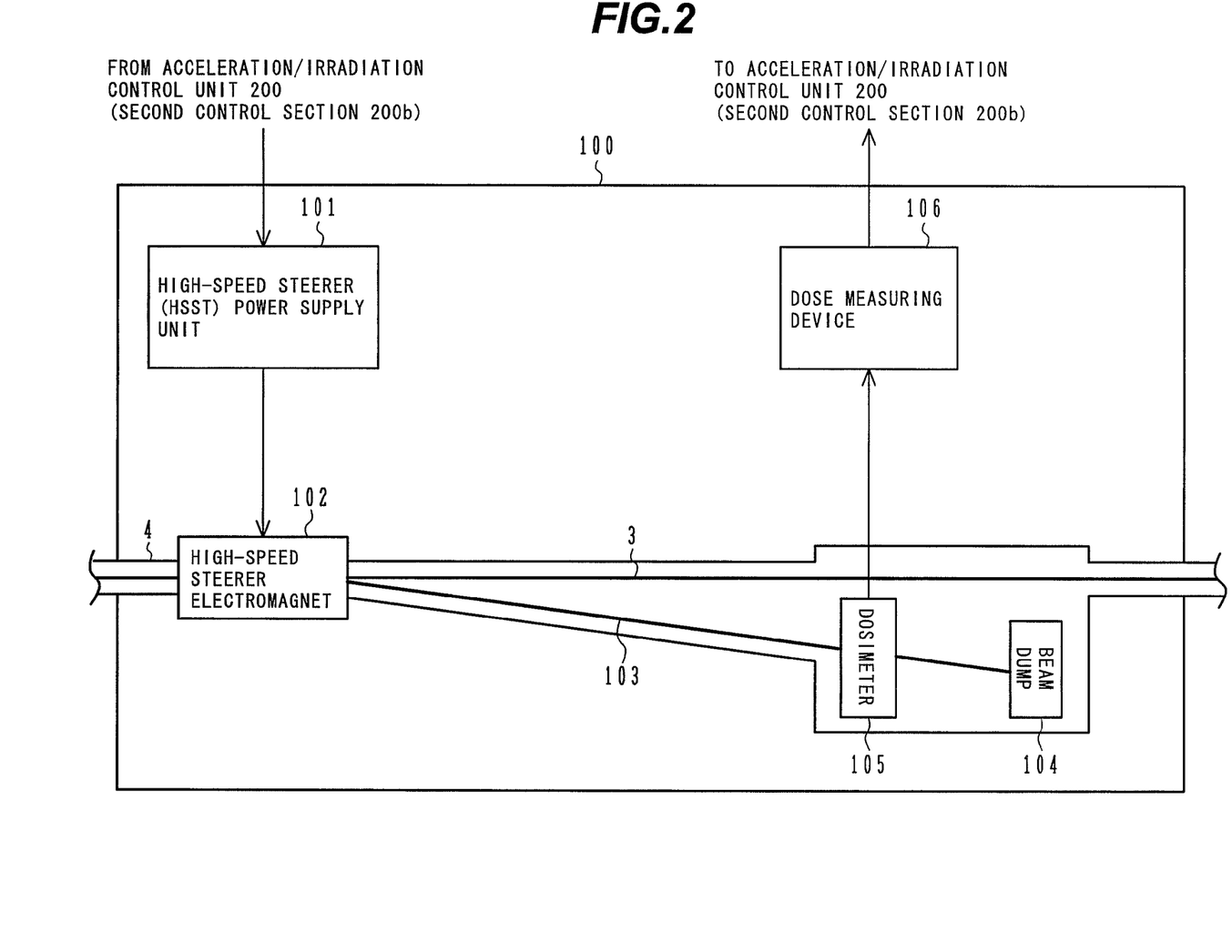
FIG. 2 is a diagram illustrating in detail a configuration of a high-speed steerer.

FIG. 2 illustrates in detail the configuration of the high-speed steerer 100.

The high-speed steerer 100 includes: a high-speed steerer (HSST) electromagnet 102 that is disposed on the beam path 3 of the first beam transport line 4; and a beam dump 104 that is disposed on a beam path 103 branching from the high-speed steerer electromagnet 102. The HSST electromagnet 102 is a steering magnet for deflecting a beam at high speed. For example, at the time of a 100% power distribution, the beam is applied to the beam dump 104. In contrast, at the time of a 0% power distribution, the beam can be sent to the subsequent beam transport lines without being deflected. Switching the high-speed steerer electromagnet 102 from the 100% to 0% power distribution and vice versa is conducted by a high-speed steerer power supply unit 101 at high speed (for example, in no more than 500 μsec). Thus, the high-speed steerer 100 can dump a beam by applying the beam to the beam dump 104 at the time of the 100% power distribution of the HSST electromagnet 102.

In addition, the high-speed steerer 100 according to the present invention further includes: a dosimeter 105 that is disposed at a position immediately before the beam dump 104 of the beam path 103; and a dose measuring device 106 that inputs a measurement signal from the dosimeter 105. A dose of a beam applied to the beam dump 104 can be measured by handling a measurement signal from the dosimeter 105 in the dose measuring device 106. Moreover, the dose measuring device 106 is capable of measuring the intensity of a beam by adding up a dose of the beam to calculate an increase in dose (the amount of change in dose value per unit time). The dosimeter 105 and the dose measuring device 106 constitute a dose monitoring device.

Next, referring to FIG. 1 again, a control system included in the charged particle beam irradiation system according to this embodiment will be described. The control system of the charged particle beam irradiation system according to this embodiment includes: a central control unit 150; the acceleration/irradiation control unit 200 that is connected to the central control unit 150; and a terminal control unit 300 that is connected to both the central control unit 150 and the acceleration/irradiation control unit 200.

The central control unit 150 reads irradiation conditions for forming an irradiation field suitable for an affected part of a patient, which are determined by a treatment planning device 450. The irradiation conditions include a beam irradiation direction, the width of SOBP, a dose, the maximum irradiation depth, and the irradiation field size. The central control unit 150 then makes a selection from among operation parameters including a kind of equipment, a placement position, an angle of placement, beam energy, a target value of the amount of beam irradiation. In addition, the central control unit 150 further includes a memory for storing information required for treatment (the information includes beam energy, an extraction radiofrequency voltage gain pattern, each rotation angle of RMW, a target dose, a rotating gantry angle, a kind of scatterer, a kind of a ridge filter, and the amount of insertion of a range shifter).

The acceleration/irradiation control unit 200 has a plurality of control sections including a first control section 200a and a second control section 200b.

The first control section 200a generates a beam extraction start signal and a beam extraction stop signal on the basis of, for example, the information stored in the memory of the central control unit 150, and RMW angle information and dose information, both of which are received from the irradiation nozzles 15A through 15D. The first control section 200a then outputs the beam extraction start signal and the beam extraction stop signal to the open/close switch 37. To be more specific, the first control section 200a forms a first control unit that controls start/stop of ion beam extraction from the synchrotron 12 on the basis of the RMW angle information and the dose information received from the irradiation nozzles 15A through 15D. Thus, the dose distribution in a target to be irradiated in an ion beam traveling direction (depth direction) can be controlled as desired by controlling start/stop of the ion beam extraction from the synchrotron 12. The above control is described in detail in JP-A-2006-239404 and JP-A-2007-222433.

In addition, the first control section 200a outputs the extraction radiofrequency voltage gain pattern, which is stored in the memory of the central control unit 150, to the voltage regulator 35 of the radiofrequency-wave supply unit 33. The voltage regulator 35 stores the extraction radiofrequency voltage gain pattern in its own memory to set the extraction radiofrequency voltage gain pattern. Moreover, the first control section 200a judges whether or not an abnormal condition has occurred at the time of beam irradiation. If it is judged that the abnormal condition has occurred at the time of beam irradiation, the first control section 200a outputs an interlock signal to the interlock switch 36.

The second control section 200b is connected to the power supply unit 101 of the high-speed steerer 100. The second control section 200b controls switching of the amount of energization of the high-speed steerer electromagnet 102 by controlling the power supply unit 101. The second control section 200b is further connected to the dose measuring device 106 of the high-speed steerer 100. The second control section 200b inputs a dose value and the beam intensity, which have been measured by the dosimeter 105 and the dose measuring device 106, and then stores (records) them in the memory. In addition, the second control section 200b outputs, to the terminal control unit 300, the dose value and the beam intensity that have been stored.

The other control sections of the acceleration/irradiation control unit 200 set parameters of the other devices including the radiofrequency cavity 32 constituting the charged-particle beam generator 1, and parameters of the control unit for controlling the other devices, on the basis of other information stored in the memory of the central control unit 150. In addition, the other control sections control these parameters.

The terminal control unit 300 includes: a monitor 300a; and an input device 300b (including a keyboard and a mouse) used for specified input through a user interface displayed in the monitor 300a. In addition, the terminal control unit 300 inputs the dose value and beam intensity received from the dose measuring device 106, both of which have been stored in the memory of the second control section 200b of the acceleration/irradiation control unit 200. The dose value and the beam intensity can be displayed on the monitor 300a. As a result, the second control section 200b of the acceleration/irradiation control unit 200 and the terminal control unit 300 constitute an irradiation management device for storing and managing the dose value and beam intensity of an ion beam. The dose value and the beam intensity have been measured by the dosimeter 105 and the dose measuring device 106 that constitute the dose monitoring device.

In addition, before the actual operation of the charged particle beam irradiation system, the beam intensity measured by the dosimeter 105 and the dose measuring device 106, which are included in the high-speed steerer 100, is inputted through the second control section 200b, and is then displayed by the terminal control unit 300. The terminal control unit 300 is used to create a voltage gain pattern to be set to the voltage regulator 35. In order to achieve this object, the terminal control unit 300 and the second control section 200b of the acceleration/irradiation control unit 200 have the following functions:

(1) when a temporary voltage gain pattern prepared beforehand is inputted, setting the voltage gain pattern to the voltage regulator 35 (first means);

(2) when an instruction to start beam extraction from the synchrotron 12 is given, starting up the voltage regulator 35 on the basis of the temporary voltage gain pattern, and controlling the steering magnet 102 so that the ion beam which has been extracted from the synchrotron 12 is applied to the beam dump 104, and then measuring an ion beam by use of the dosimeter 105 and the dose measuring device 106 (dose monitoring device) (second means);

(3) displaying a dose value of an ion beam measured by the dose monitoring device (third means);

(4) when an instruction to adjust the temporary voltage gain pattern is inputted, adjusting the temporary voltage gain pattern, and then setting the adjusted voltage gain pattern to the voltage regulator 35 again (fourth means).

To be more specific, the terminal control unit 30 and the second control section 200b of the acceleration/irradiation control unit 200 constitute an voltage gain pattern creation device for creating an voltage gain pattern to be set to the voltage regulator 35 by use of measured values obtained by the dosimeter 105 and the dose measuring device 106 that constitute the dose monitoring device.

Next, operation according to this embodiment will be described.

Figure 3A:
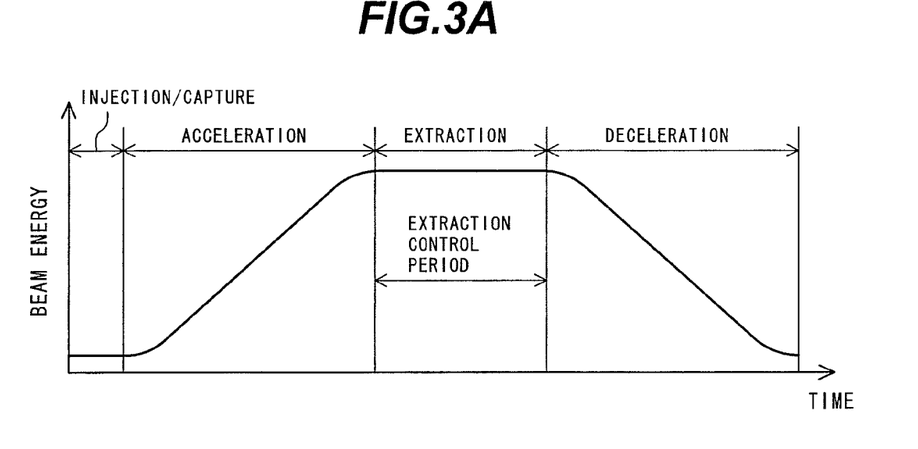
FIG. 3A illustrates a change in beam energy in one operation cycle of the synchrotron.

As shown in FIG. 3A, when the synchrotron 12 is operated, the synchrotron 12 repeats the steps of: injecting/capturing an ion beam; accelerating the ion beam up to the set energy; extracting the ion beam whose energy has been increased to a target value; and decelerating the ion beam. How to control the injection/capture, the acceleration, the extraction, and the deceleration (in other words, one operation cycle of the synchrotron 12) is specified according to the energy of an ion beam to be accelerated. An ion beam, which is orbiting around a closed orbit of the synchrotron 12, is accelerated up to target energy. After that, during a period of the extraction, the radiofrequency-wave supply unit 33 is started up to operate the radiofrequency-wave applicator 31 so that an extraction radiofrequency wave is applied. As a result, an ion beam is extracted from the synchrotron 12 into the first beam transport line 4. This enables the synchrotron 12 to supply, during an extraction control period, the ion beam to the irradiation nozzles 15A through 15D of the treatment rooms 2A through 2D that are connected to subsequent second beam transport lines 5A through 5D respectively.

Figure 3B:
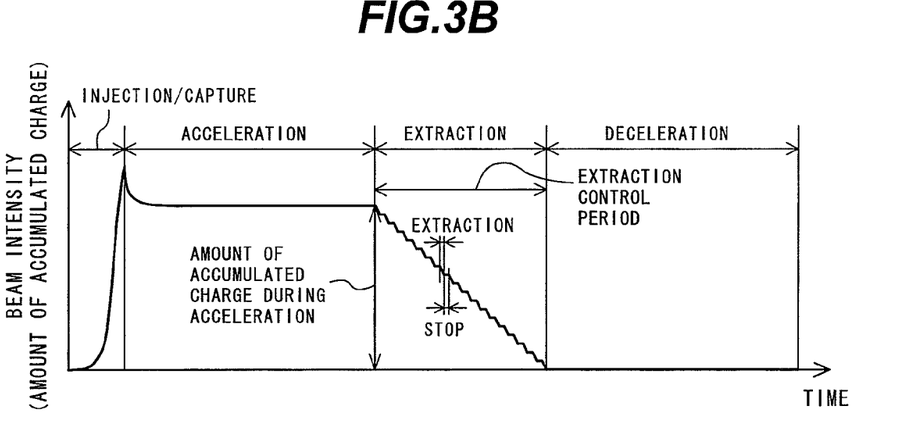
FIG. 3B illustrates a change in intensity of a beam orbiting the synchrotron in one operation cycle of the synchrotron.

As shown in FIG. 3B, the beam intensity of an ion beam orbiting the ion beam orbiting synchrotron 12 (the amount of accumulated electric charge of an orbiting beam) changes in response to the operation of the synchrotron 12 (shown in FIG. 3A). When an ion beam is injected into the synchrotron 12 so that the synchrotron 12 captures the ion beam, the beam intensity is gradually increased. In an early stage of the acceleration control, a space-charge effect, and the like, cause a loss of the ion beam, which results in the attenuation of the beam intensity. However, the beam intensity is kept substantially constant during a period ranging from a middle stage to a late stage of the acceleration control. Because the beam intensity at the end of the acceleration is equivalent to the amount of accumulated electric charge in the synchrotron 12, the extraction of an ion beam from the synchrotron 12 causes the intensity of an orbiting beam to gradually attenuate. According to this embodiment, the extraction of an ion beam is repeatedly started and stopped. Accordingly, the beam intensity also changes in a step-like manner. This is because an ion beam is supplied to the outside of the synchrotron 12 by the ion-beam extraction control, which causes the intensity of the orbiting ion beam to attenuate, whereas while the extraction control is stopped, the ion beam is not supplied to the outside of the synchrotron 12, which does not cause the intensity of the orbiting ion beam to attenuate. The ion beam remaining in the synchrotron 12, which has not been completely extracted during the extraction control period, is decelerated down to the low energy, and is then extinguished, by the subsequent speed reduction control.

Figure 3C:
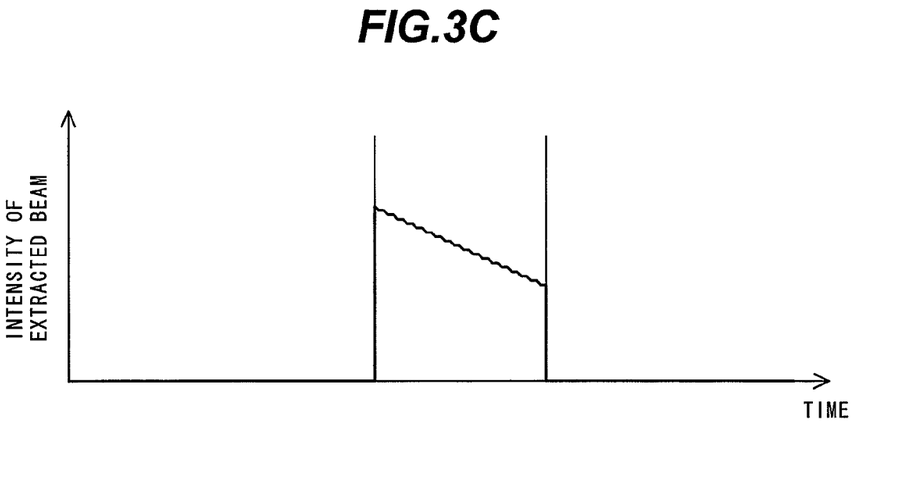
FIG. 3C illustrates a change in intensity of an ion beam extracted during an extraction control period.
Figure 4:
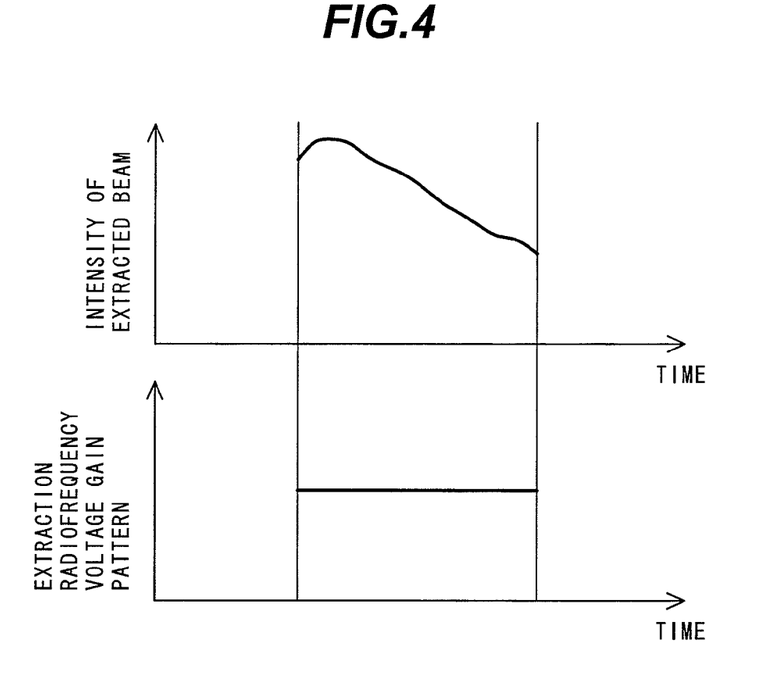
FIG. 4 is a diagram illustrating the relationship between such a gain pattern for an extraction radiofrequency voltage that an extraction radiofrequency applied is kept constant (that is to say, a gain of the voltage is kept constant) and the intensity of the extracted ion beam based on the extraction radiofrequency voltage gain pattern.

As shown in FIG. 3C, the beam intensity of an ion beam which has been extracted from the synchrotron 12 into the first beam transport line 3 usually has a time structure (characteristics that change with the lapse of time). A change in intensity of an extracted ion beam shown in FIG. 3C is obtained when an extraction radiofrequency voltage gain pattern is set to the voltage regulator 35 of the radiofrequency-wave supply unit 33 such that an extraction radiofrequency voltage is kept constant (that is to say, a gain of the voltage is kept constant) as shown in FIG. 4. To be more specific, because the intensity of an ion beam orbiting in the synchrotron 12 is high in an early stage of the extraction, the intensity of an ion beam extracted from the synchrotron 12 is also high. However, as the intensity of the ion beam orbiting in the synchrotron 12 attenuates as a result of the extraction of the ion beam as shown in FIG. 3B, the intensity of the ion beam extracted from the synchrotron 12 also tends to gradually decrease in point of time if the extraction radiofrequency voltage is kept constant.

Figure 5:
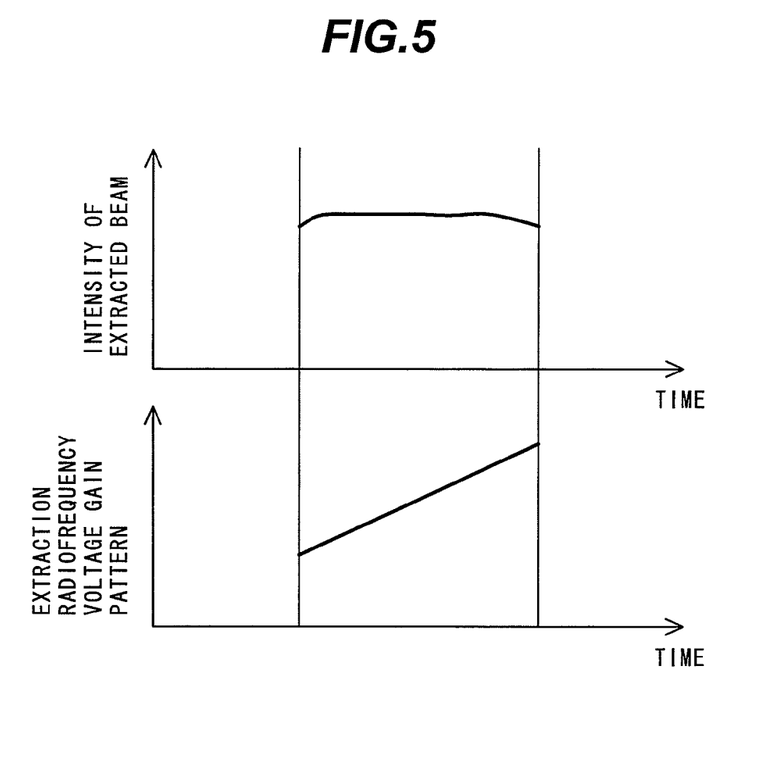
FIG. 5 is a diagram illustrating the relationship between such an extraction radiofrequency voltage gain pattern that an extraction radiofrequency voltage gradually increases (that is to say, a gain of the voltage gradually increases) and the intensity of the extracted ion beam based on the extraction radiofrequency voltage gain pattern.

In contrast, as shown in FIG. 5, the intensity of an extracted ion beam can be kept constant by increasing the extraction radiofrequency voltage in point of time by use of a gain pattern in which the extraction radiofrequency voltage gain, which is set to the voltage regulator 35 of the radiofrequency-wave supply unit 33, is gradually increased.

Heretofore, an extraction radiofrequency voltage gain pattern is adjusted by measuring dose values from dosimeters disposed in the irradiation nozzles 15A through 15D of the treatment rooms 2A through 2D respectively.

According to the present invention, the use of the synchrotron 12, the first beam transport line 3, and the high-speed steerer 100 enables the adjustment of an ion beam extracted from the synchrotron 12.

To be more specific, 100% energization of the high-speed steerer electromagnet 102 is performed to apply an ion beam to the beam dump 104; and the intensity of the extracted ion beam is then measured by the dosimeter 105 and the dose measuring device 106 that are disposed immediately before the beam dump 104. This makes it possible to adjust an extraction radiofrequency voltage gain pattern that is set to the voltage regulator 35 of the radiofrequency-wave supply unit 33 as shown in FIG. 5, and thereby to keep the intensity of the ion beam extracted from the synchrotron 12 constant.

Adjustment steps for adjusting an extraction radiofrequency voltage gain pattern according to this embodiment will be described as below.

First, a temporary voltage gain pattern prepared beforehand is inputted by using the monitor 300a and the input device 300b that are included in the terminal control unit 300. The temporary voltage gain pattern is then set to the voltage regulator 35 through the second control section 200b of the acceleration/irradiation control unit 200. Next, an ion beam is introduced into the synchrotron 12 from the pre-accelerator 11. The ion beam is then accelerated up to the desired energy in the synchrotron 12. After that, during an extraction control period of an operation cycle of the synchrotron 12, the monitor 300a and the input device 300b, which are included in the terminal control unit 300, are used to give an instruction to start beam extraction from the synchrotron 12. On the receipt of the instruction, the second control section 200b of the acceleration/irradiation control unit 200 operates the voltage regulator 35 to which the temporary voltage gain pattern has been set, and concurrently with this, controls the high-speed steerer power supply unit 101 so that an ion beam which has been extracted from the synchrotron 12 at this point of time is applied to the beam dump 104 of the high-speed steerer 100, and so that the dosimeter 105 and the dose measuring device 106 measure the ion beam. At this time, the second control section 200b inputs a dose value and the beam intensity that have been measured by both the dosimeter 105 and the dose measuring device 106, and then stores (records) them in the memory. Concurrently with the above operation, the second control section 200b outputs the beam intensity to the terminal control unit 300. The terminal control unit 300 displays the beam intensity data as numerical values or using a graph (for example, using a graph of a function of time as shown in the upper part of FIG. 4) on the monitor 300a. An operator makes a judgment from the beam intensity data displayed in the monitor 300a as to whether or not it is necessary to adjust a voltage gain pattern. If it is judged that the adjustment is required, the operator adjusts the temporary voltage gain pattern by use of the monitor 300a and the input device 300b that are included in the terminal control unit 300. As a result, the adjusted voltage gain pattern is set to the voltage regulator 35 again through the second control section 200b of the acceleration/irradiation control unit 200. The repetition of the above-described steps makes it possible to adjust the extraction radiofrequency voltage gain pattern, which is set to the voltage regulator 35 of the radiofrequency-wave supply unit 33, to a desired pattern, and thereby to keep the intensity of the ion beam extracted from the synchrotron 12 constant.

According to this embodiment that is configured as described above, the following effects are produced.

Heretofore, the intensity of an ion beam extracted from the synchrotron 12 is measured by use of dose values from dosimeters disposed in the irradiation nozzles 15A through 15D of the treatment rooms 2A through 2D respectively. Therefore, an extraction radiofrequency voltage gain pattern is adjusted by performing measurement using a dosimeter at the end with the original intensity of an ion beam extracted from the synchrotron 12 kept unknown. As a result, the acquired extraction radiofrequency voltage gain pattern is influenced by various devices existing on the way to the irradiation nozzles 15A through 15D of the treatment rooms 2A through 2D.

According to this embodiment, the measurement by the dosimeter 105 and the dose measuring device 106, which are included in the high-speed steerer 100, makes it possible to adjust an extraction radiofrequency voltage gain pattern, and to perform accurate adjustment with fluctuation factors of the intensity of an extracted ion beam correctly kept track of.

In addition, when an extracted ion beam fluctuates for some unexpected reason, a fluctuation factor thereof can be identified. More specifically, it is possible to judge whether the fluctuation factor exists in the synchrotron 12 or in the other elements including the first beam transport line 4, the second beam transport lines 5A through 5D, the irradiation nozzles 15A through 15D, and other devices. Therefore, saving of time taken to cope with the fluctuation factor, and an improvement in accuracy, can be expected.

Moreover, in a construction stage of a charged particle beam irradiation system, the intensity of an ion beam extracted from the synchrotron 12 can be adjusted without waiting until the construction of the charged particle beam irradiation system is completed. This enables early startup of the charged particle beam irradiation system.

A second embodiment of the present invention will be described with reference to FIGS. 6 through 8.

Figure 6:
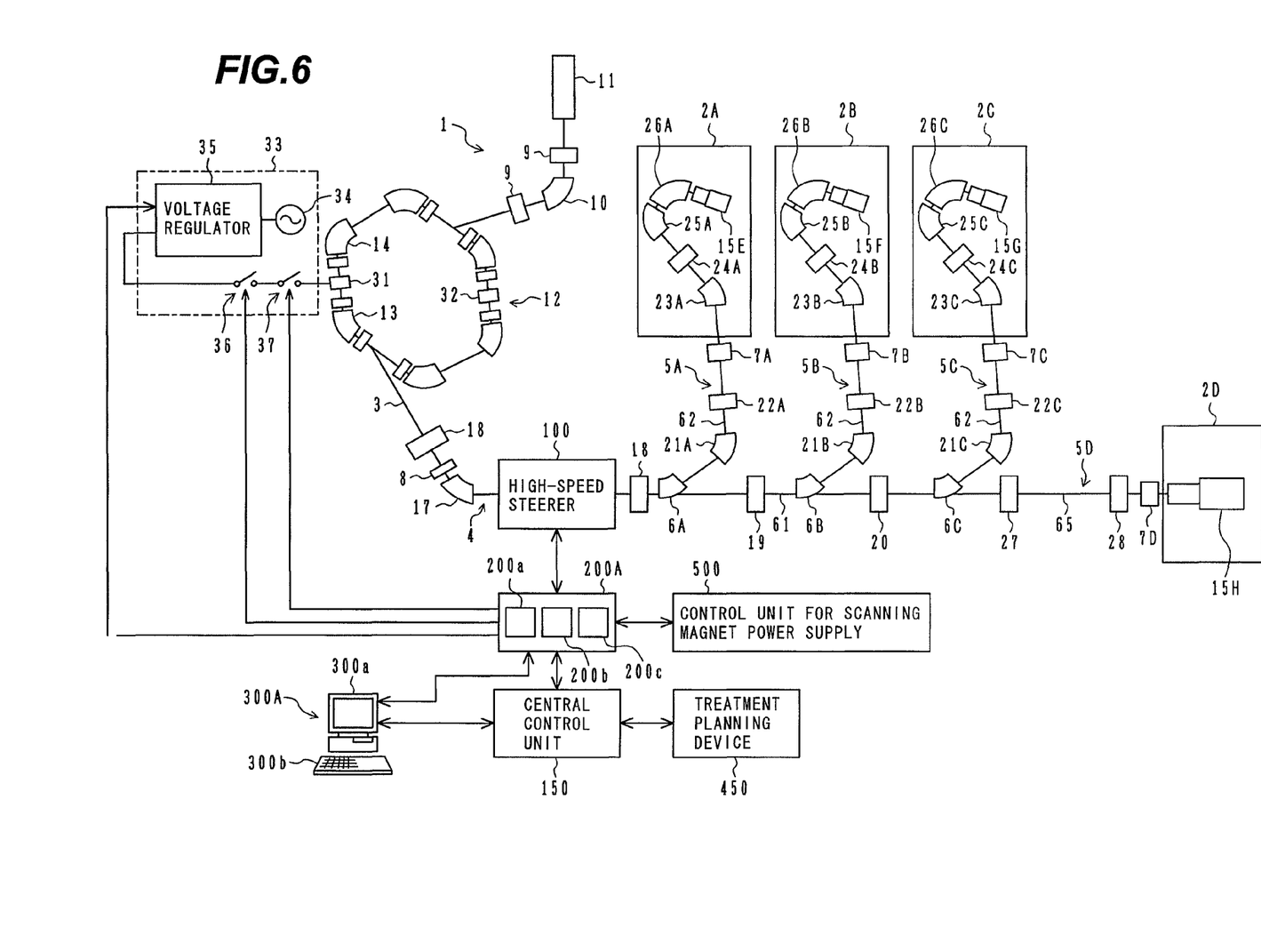
FIG. 6 is a diagram schematically illustrating an overall configuration of a charged particle beam irradiation system according to a second embodiment of the present invention.

FIG. 6 is a diagram illustrating an overall configuration of a charged particle beam irradiation system according to this embodiment. Similar reference numerals are used in FIG. 6 to designate parts that are similar to those shown in FIG. 1. In this embodiment, the present invention is applied to a system that uses beam scanning irradiation, particularly to a system that uses a spot scanning irradiation method in which an affected part is irradiated with an ion beam.

According to this embodiment, the charged particle beam irradiation system includes irradiation nozzles 15E through 15H, each of which has a scanning magnet. A control unit 500 for a scanning magnet power supply controls a scanning magnet power supply, which is not illustrated, so as to control an excitation current. As a result, each of the irradiation nozzles 15E through 15H scans an ion beam in a lateral direction. In addition, each of irradiation nozzles 15E through 15H stops movement (scanning) of an ion beam at each irradiation position before irradiation. When a dose at the irradiation position reaches a target value, a move to the next irradiation position is made. While the move to the next irradiation position is made, the extraction of the ion beam from the synchrotron 12 is kept stopped. On the completion of the move to the next irradiation position, an ion beam is extracted from the synchrotron 12 again. In order to carry out the scanning magnet control and the ion-beam ON/OFF control as described above, each of the irradiation nozzles 15E through 15H includes: a dosimeter for detecting a dose (radiation amount) of an ion beam; and a position detector for detecting an irradiation position. The dose information and the positional information are output to the acceleration/irradiation control unit 200A.

Moreover, as a control system, the charged particle beam irradiation system according to this embodiment further includes a central control unit 150A, an acceleration/irradiation control unit 200A, a terminal control unit 300A, and a scanning magnet power supply control unit 500.

The acceleration/irradiation control unit 200A has a plurality of control sections including a first control section 200a, a second control section 200b, and a third control section 200c.

The first control section 200a generates a beam extraction start signal and a beam extraction stop signal on the basis of, for example, information stored in the memory of the central control unit 150A, and the dose information and the positional information, both of which are received from the irradiation nozzles 15E through 15H. The first control section 200a then outputs the beam extraction start signal and the beam extraction stop signal to the open/close switch 37 to control start/stop of ion beam extraction from the synchrotron 12 (first control unit). The third control section 200c determines an excitation current of a scanning magnet, which is used to make a move to the next irradiation position, on the basis of, for example, the information stored in the memory of the central control unit 150A, and the dose information and the positional information, both of which are received from the irradiation nozzles 15E through 15H. The third control section 200c then outputs the excitation current information to the scanning magnet power supply control unit 500. The scanning magnet power supply control unit 500 controls the scanning magnet power supply, which is not illustrated, on the basis of the excitation current information so that an excitation current of the scanning magnet is controlled. Thus, an excitation current of the scanning magnet as well as start/stop of ion beam extraction from the synchrotron 12 is controlled. As a result, an ion beam can be scanned in a lateral direction in a target to be irradiated (in a direction perpendicular to an ion beam traveling direction (depth direction)). This makes it possible to control the dose distribution in the lateral direction as desired. This control is described in detail in Japanese Patent No. 2833602.

The other functions of the first control section 200a are the same as those of the first control section 200a in the first embodiment.

The second control section 200b and the terminal control unit 300A have functions similar to those of the second control section 200b and the terminal control unit 300 in the first embodiment.

In addition, the second control section 200b according to this embodiment has the following functions:

(1) in synchronization with start/stop of ion beam extraction from the synchrotron 12, controlling the excitation of the steering magnet 102 so that a leaking beam (described later) occurring when the ion beam extraction is stopped is applied to the beam dump 104, and then measuring the leaking beam by use of the dosimeter 105 and the dose measuring device 106 (the dose monitoring device) (second control unit);

(2) before the control of the extraction in an operation cycle of the synchrotron 12, extracting, as a dumped beam (described later), part of an ion beam accumulated in the synchrotron 12, and concurrently with this, controlling the excitation of the steering magnet 102 so that the dumped beam extracted from the synchrotron 12 is applied to the beam dump 104, and then measuring the dumped beam by use of the dose monitoring device (third control unit);

(3) on the basis of a dose value of the leaking beam or that of the dumped beam, both of which have been measured by the dose monitoring device, correcting an extraction radiofrequency voltage gain pattern that is set to the voltage regulator 35 (voltage gain pattern correction unit).

Moreover, the second control section 200b and the terminal control unit 300A function as an irradiation management device for managing a dose value of the leaking beam or that of the dumped beam, both of which have been measured by the dose monitoring device.

Figure 7A:
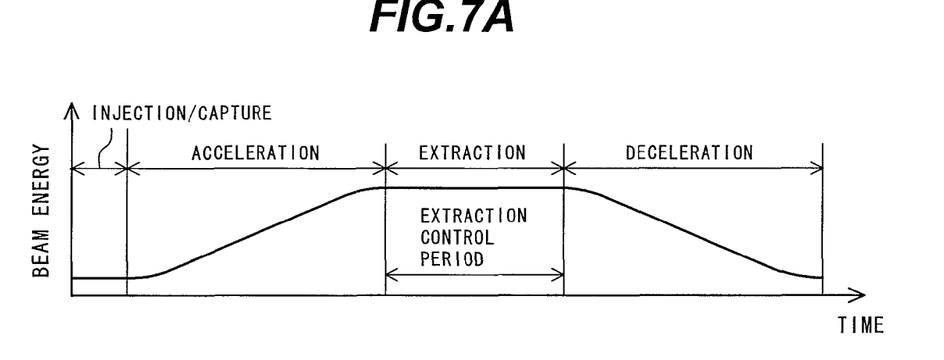
FIG. 7A illustrates a change in beam energy in one operation cycle of the synchrotron.
Figure 7B:
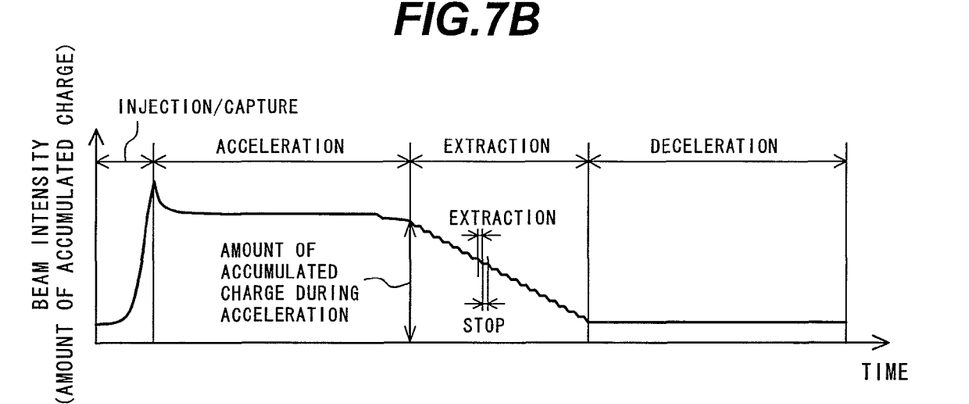
FIG. 7B illustrates a change in intensity of a beam orbiting the synchrotron in one operation cycle of the synchrotron.
Figure 7C:
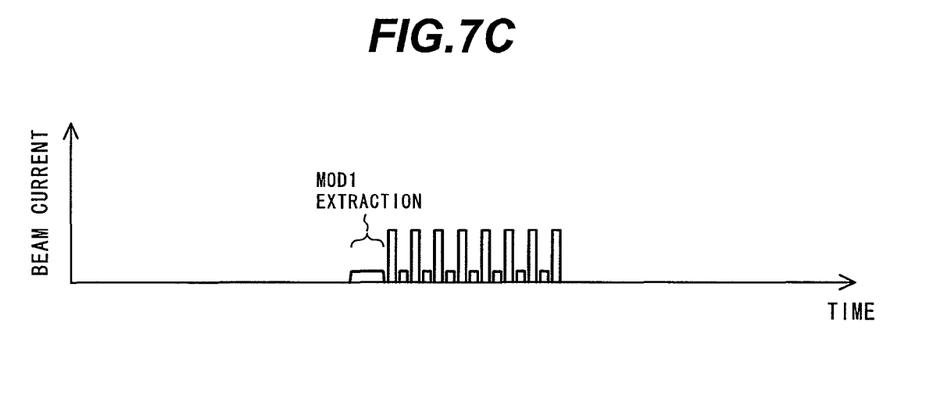
FIG. 7C illustrates a dumped beam before the start of the control during an extraction control period, an ion beam by spot irradiation during the extraction control period, and a current value of a leaking beam occurring when the extraction is stopped during the extraction control period.
Figure 8:
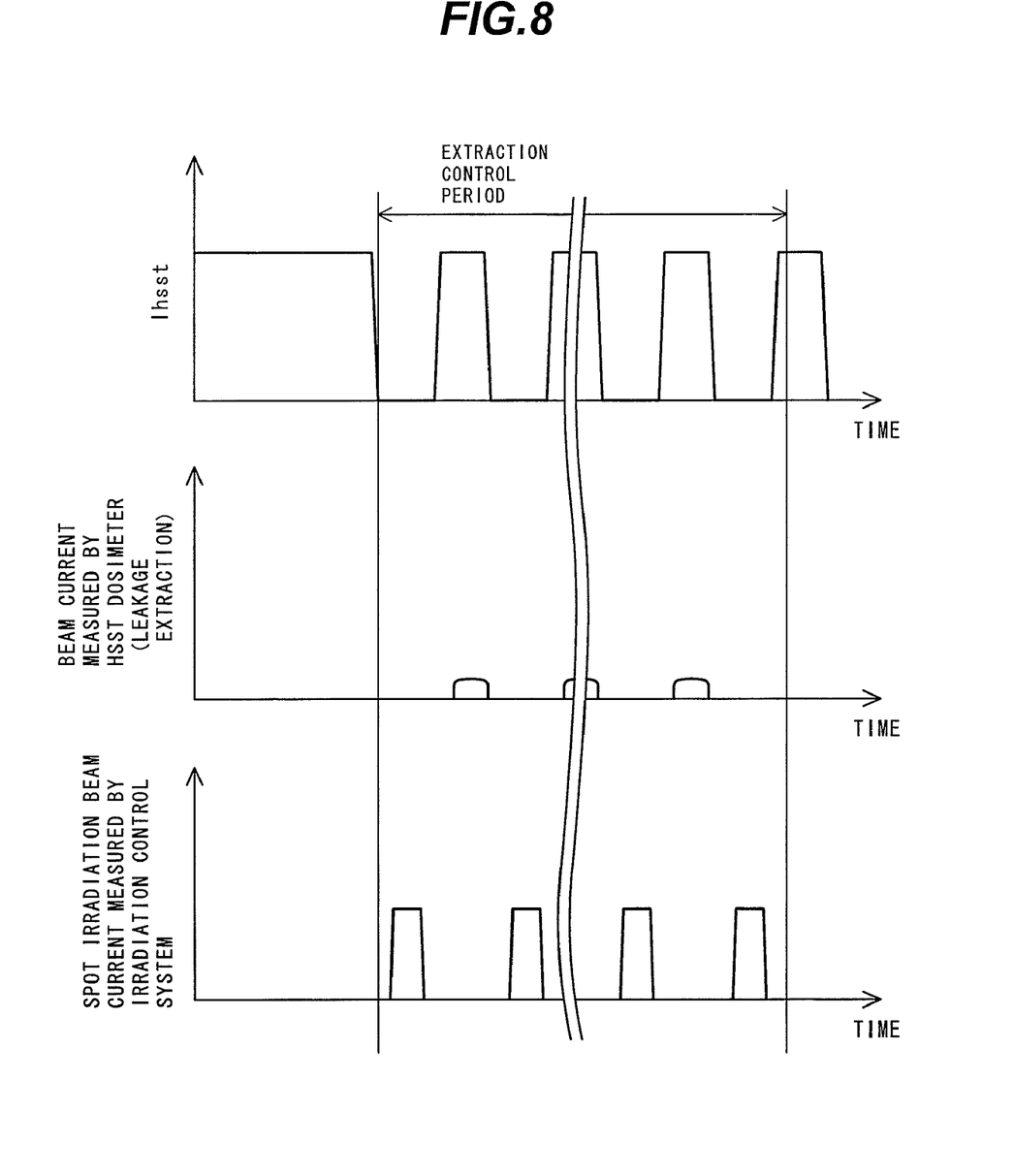
FIG. 8 is a diagram illustrating: a control current value of a steering magnet in a high-speed steerer based on spot irradiation during an extraction control period (upper chart); a current value of a leaking beam measured by a dosimeter in the high-speed steerer (central chart); and a beam current value by spot irradiation measured by a dosimeter in an irradiation nozzle (lower chart).

FIGS. 7A through 7C are charts each illustrating how the synchrotron 12 operates in one operation cycle when irradiation with an ion beam is carried out by means of spot scanning. More specifically, FIG. 7A illustrates a change in beam energy in one operation cycle of the synchrotron 12; FIG. 7B illustrates a change in intensity of a beam orbiting the synchrotron 12 in one operation cycle of the synchrotron 12; and FIG. 7C illustrates a dumped beam before the start of the control during an extraction control period, an ion beam by spot irradiation during the extraction control period, and a current value of a leaking beam when the extraction is stopped during the extraction control period. FIG. 8 is a diagram illustrating: a control current value of the steering magnet 102 in the high-speed steerer 100 based on spot irradiation during an extraction control period (upper chart); a current value of a leaking beam measured by the dosimeter 105 in the high-speed steerer 100 (central chart); and a beam current value by spot irradiation measured by the dosimeter in the irradiation nozzle (lower chart).

when irradiation with an ion beam is carried out by means of spot scanning, an ion beam accumulated in the synchrotron 12 may be intentionally extracted before the start of the control during an extraction control period, and then the ion beam may be dumped by use of the high-speed steerer 100 without transporting the ion beam to the irradiation nozzles 15E through 15H.

In this case, before the start of the extraction control, the ion beam is extracted from the synchrotron 12 as a dumped beam. Accordingly, the amount of accumulated electric charge of the synchrotron 12 decreases to a corresponding degree. As shown in FIGS. 7B, 7C, after the end of the acceleration, and before the start of the extraction control, the amount of electric charge of the synchrotron 12 is kept at a certain constant value. However, because a dumped beam is intentionally extracted, the amount of electric charge before the start of the extraction control decreases.

According to this embodiment, the second control section 200b and the terminal control unit 300A, which function as the third control unit and the irradiation management device, instruct the dosimeter 105 and the dose measuring device 106, which are included in the high-speed steerer 100, to measure the amount of electric charge that has decreased because of the dumped beam, and then display the amount of electric charge on the monitor 300a of the terminal control unit 300A. This makes it possible to evaluate the amount of electric charge, and to manage the amount of irradiated dose in a subsequent extraction period.

In addition, as shown in FIG. 7C, at the time of the spot irradiation during the extraction control period, the radiofrequency-wave supply unit 33 is controlled so that an extraction radiofrequency wave is applied, which causes an ion beam to be extracted from the synchrotron 12. However, in this extraction control period, even if the extraction radiofrequency wave is not applied, a leaking beam is slightly extracted from the synchrotron 12. At this time, according to this embodiment, the second control section 200b, which functions as the second control unit, performs 100% energization of the steering magnet 102 in synchronization with the stop of the ion beam extraction from the synchrotron 12 as shown in the upper chart of FIG. 8 so that the leaking beam is applied to the beam dump 104. This makes it possible to prevent irradiation with an unnecessary ion beam. Moreover, the second control section 200b and the terminal control unit 300A, which function as the third control unit and the irradiation management device, measure a dose of the leaking beam by use of the dosimeter 105, and then display a dose of the leaking beam on the monitor 300a of the terminal control unit 300A. As a result, dose management can be more accurately performed.

When the spot scanning irradiation is performed, a dose is managed on a spot basis, and irradiation with an ion beam is carried out with a spot position scanned. The number of spots which can be irradiated by the synchrotron 12 is determined by the amount of accumulated charge accelerated by the synchrotron 12. However, as described above, the amount of irradiated dose which can be subjected to spot irradiation can be finely managed by monitoring a dose of a dumped beam that is intentionally dumped before the extraction control period, and by monitoring a dose of a leaking beam occurring between spot irradiations during the extraction control period. This makes it possible to irradiate with an ion beam accelerated by the synchrotron 12 without waste, and thereby to improve the irradiation efficiency without lacking in the amount of electric charge.

Further, as described above, if an ion beam is intentionally dumped as a dumped beam before the extraction control period, or if a leaking beam occurs between spot irradiations during the extraction control period, the intensity of an ion beam orbiting the synchrotron 12 decreases to a corresponding degree. This means that the intensity of the ion beam orbiting the synchrotron 12 deviates from the beam intensity which has been expected at the time of the creation of the extraction radiofrequency voltage gain pattern set to the voltage regulator 35. Therefore, if the extraction radiofrequency voltage gain pattern is used just as it is to control the extraction radiofrequency voltage, the intensity of the extraction beam cannot be uniformly controlled.

According to this embodiment, because the second control section 200b functions as the voltage gain pattern correction unit, the extraction radiofrequency voltage gain pattern which is set to the voltage regulator 35 is automatically corrected on the basis of the dose value of the leaking beam or of the dumped beam, which has been measured by the dose monitoring device. As a result, the intensity of an extracted ion beam can be kept constant without being influenced by the leaking beam and the dumped beam.

What is claimed is:

1. A charged particle beam irradiation system comprising:
a charged particle beam generator for accelerating and extracting a charged particle beam;
a beam transport line for transporting the charged particle beam extracted from the charged particle beam generator, said beam transport line being connected to the charged particle beam generator; and
at least one irradiation nozzle for irradiating an affected part of a patient with the charged particle beam; wherein
said charged particle beam irradiation system further comprises:
a beam dump device including: a steering magnet that is disposed on the beam transport line; and a beam dump that is disposed on a beam path branching from the steering magnet, said beam dump device performing the excitation control of the steering magnet such that from among charged particle beams extracted from the charged particle beam generator, a charged particle beam which is not to be transported to the irradiation nozzle is applied to the beam dump; and
a dose monitoring device disposed in the beam dump device for measuring the dose of the charged particle beam applied to the beam dump.

2. The charged particle beam irradiation system according to claim 1, further comprising an irradiation control device for storing and managing the dose of a charged particle beam measured by the dose monitoring device.

3. The charged particle beam irradiation system according to claim 1, wherein:
said charged particle beam generator includes:
a synchrotron;
a radiofrequency-wave applicator located in the synchrotron for applying an radiofrequency wave to a charged particle beam orbiting in the synchrotron; and
a voltage regulator for controlling a radiofrequency voltage to be supplied to the radiofrequency-wave applicator on the basis of a predetermined gain pattern of the radiofrequency voltage and for controlling the intensity of a charged particle beam extracted from the synchrotron to the beam transport line; and
said dose monitoring device measures the dose of a charged particle beam which is not to be transported to the irradiation nozzle, from among charged particle beams extracted from the synchrotron.

4. The charged particle beam irradiation system according to claim 3, further comprising a voltage gain pattern creation device for creating a voltage gain pattern to be set for the voltage regulator by use of a measured value by the dose monitoring device.

5. The charged particle beam irradiation system according to claim 4, wherein
said voltage gain pattern creation device includes:
first means for setting a beforehand-prepared, temporary voltage gain pattern for the voltage regulator when the temporary voltage gain pattern is input;
second means for operating the voltage regulator on the basis of the temporary voltage gain pattern when an instruction to start beam extraction from the synchrotron is given, for controlling the steering magnet so that a charged particle beam extracted from the synchrotron at the time of the operation is applied to the beam dump, and for measuring the dose of the charged particle beam by use of the dose monitoring device;
third means for displaying the dose of the charged particle beam measured by the dose monitoring device; and
fourth means for adjusting the temporary voltage gain pattern when instructed to do so and then setting the adjusted voltage gain pattern for the voltage regulator.

6. The charged particle beam irradiation system according to claim 3, further comprising:
a first control unit for controlling the start and stop of charged particle beam extraction from the synchrotron;
a second control unit for controlling the excitation of the steering magnet in synchronization with the start and stop of the charged particle beam extraction from the synchrotron and for applying to the beam dump a leaking beam occurring when the charged particle beam extraction is stopped to measure the dose of the leaking beam by use of the dose monitoring device; and
an irradiation control device for managing the dose of the leaking beam measured by the dose monitoring device.

7. The charged particle beam irradiation system according to claim 3, further comprising:
a first control unit for controlling the start and stop of charged particle beam extraction from the synchrotron;
a second control unit for controlling the excitation of the steering magnet in synchronization with the start and stop of the charged particle beam extraction from the synchrotron and for applying to the beam dump a leaking beam occurring when the charged particle beam extraction is stopped to measure the dose of the leaking beam by use of the dose monitoring device; and
a voltage gain pattern correction unit for correcting, on the basis of the dose of the leaking beam measured by the dose monitoring device, the gain pattern of the radiofrequency voltage set for the voltage regulator.

8. The charged particle beam irradiation system according to claim 3, further comprising:
a third control unit for extracting, as an unnecessary beam, part of charged particle beams accumulated in the synchrotron before beam extraction control is started during an extraction control period in an operation cycle of the synchrotron and for controlling simultaneously the excitation of the steering magnet so that the unnecessary beam extracted from the synchrotron is applied to the beam dump to measure the dose of the unnecessary beam by use of the dose monitoring device; and
an irradiation control device for managing the dose of the unnecessary beam measured by the dose monitoring device.

9. The charged particle beam irradiation system according to claim 3, further comprising:
a third control unit for extracting, as an unnecessary beam, part of charged particle beams accumulated in the synchrotron before beam extraction control is started during an extraction control period in an operation cycle of the synchrotron and for controlling simultaneously the excitation of the steering magnet so that the unnecessary beam extracted from the synchrotron is applied to the beam dump to measure the dose of the unnecessary beam by use of the dose monitoring device; and
a voltage gain pattern correction unit for correcting, on the basis of the dose of the unnecessary beam measured by the dose monitoring device, the gain pattern of the radiofrequency voltage set for the voltage regulator.

* * * * *